United States Patent [19]

Malata, Jr.

[11] Patent Number: 5,074,785
[45] Date of Patent: Dec. 24, 1991

[54] ANGLE PIECE COUPLING

[75] Inventor: Peter Malata, Jr., Bürmoos, Austria

[73] Assignee: Dentalwerk Bürmoos Gesellschaft m.b.H., Bürmoos, Austria

[21] Appl. No.: 439,269

[22] Filed: Nov. 20, 1989

[30] Foreign Application Priority Data

Nov. 21, 1988 [AT] Austria .................. 2854/88

[51] Int. Cl.$^5$ .................................. A61C 3/08
[52] U.S. Cl. ........................... 433/29; 433/126
[58] Field of Search ........................ 433/29, 126

[56] References Cited

U.S. PATENT DOCUMENTS

| 4,600,384 | 7/1986 | Olsen | 433/29 |
| 4,655,709 | 4/1987 | Fleer | 433/29 |
| 4,669,982 | 6/1987 | Fleer | 433/29 |

FOREIGN PATENT DOCUMENTS 0075096 1/1981 European Pat. Off. .
0143985 1/1983 European Pat. Off. .

Primary Examiner—John J. Wilson
Attorney, Agent, or Firm—Toren, McGeady & Associates

[57] ABSTRACT

The invention is directed to a coupling for connecting dental angle pieces with handpieces. In so doing, an outlet point for the light guide 14 is provided in the angle piece near the tool holder in order to illuminate the work place in the mouth of the patient. The corresponding light source is provided either in the angle piece or in the handpiece, wherein the light is arranged on a slip ring on the coupling side when this light is on the angle piece side. The slip ring which carries the light source when the latter is contained in the angle piece is exchangeable for a ring which has a continuous light guide in place of the light, and a nose is likewise provided in this ring at the same location of the nose on the angle pieces which do not have a light.

2 Claims, 3 Drawing Sheets

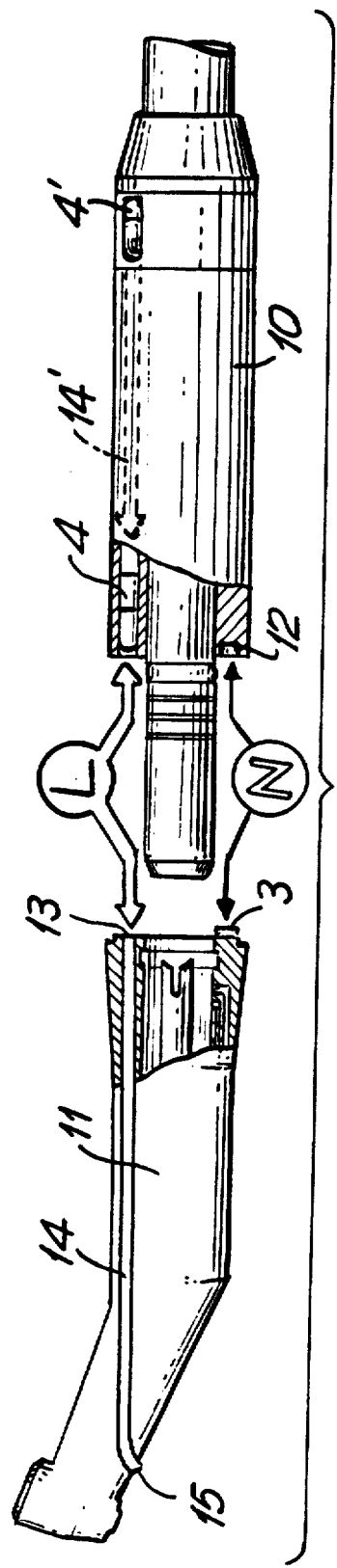
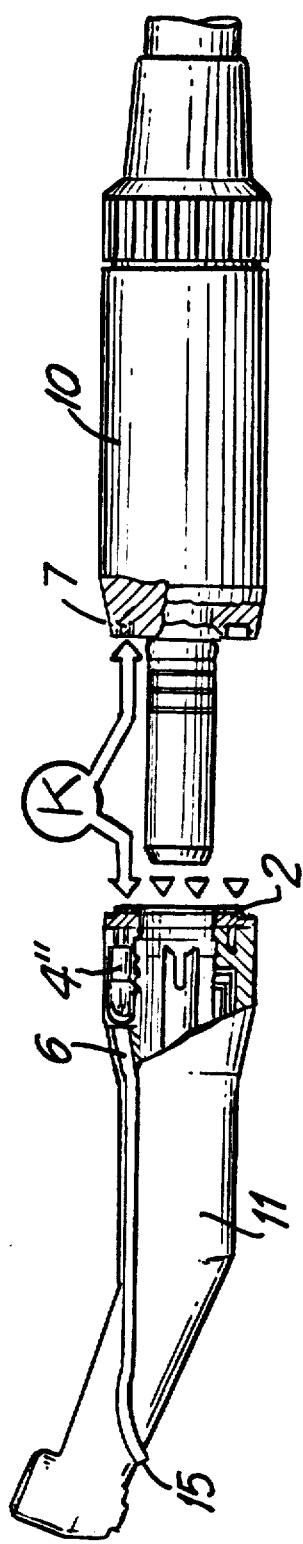

ANGLE PIECE COUPLING

BACKGROUND OF THE INVENTION

The invention is directed to a coupling for connecting dental angle pieces with dental handpieces, wherein an outlet point for a light guide is provided near the tool holder in order to illuminate the work place in the mouth of the patient. A corresponding light source being provided either in the angle piece or in the handpiece.

A whole series of dental angle pieces with such light guides are known, but two types have proven to be successful in practice.

In a first known system, the light source is located in the handpiece and the light receiving end of the light guide is located in the angle piece opposite the light source. In order to secure this opposite location, a nose is provided in the coupling, which in other respects is symmetrical with respect to rotation. The nose ensures a correct angular position between the angle piece and the handpiece.

In a second commonly occurring system, the light source is located in the angle piece and is provided with current from the handpiece by means of concentric, circular slip rings at the end face of the coupling regardless of the angular position between the angle piece and the handpiece.

The existence of these known illumination systems brings about a whole series of disadvantages for both the producer of the angle pieces and the dentist. The handpieces are usually manufactured by companies which also produce the patient chairs for dental practices. The producers of the angle pieces generally do not manufacture dental chairs, and the producers of the chairs, in turn, generally do not manufacture angle pieces. The producers of the angle pieces must accordingly take into account the two different systems in production and storage and are compelled to expand their storage space. Of course, this has a disadvantageous effect on costs and delivery times.

The users, in turn, are constrained in the selection of the angle pieces by the handpiece system which they have selected and, if connections for both types of handpieces are provided in their work place, must be very careful not to confuse the corresponding handpieces and, when changing the angle piece, must often change the handpiece as well. This, in turn, is cumbersome and results in problems with the sterilization of the instruments after treating a patient.

SUMMARY OF THE INVENTION

Accordingly, it is an object of the present invention to avoid these disadvantages and to provide a connection of the above-mentioned type which is usable for both systems with as little retooling work as possible. The dentist using this should also be able to carry out this retooling, at least when deciding which angle pieces he will use with which handpieces, if not already during the treatment of the patient.

Pursuant to this object, and others which will become apparent hereafter, one aspect of the present invention resides in that the slip ring, which carries the light source when the latter is contained in the angle piece, can be exchanged with a second ring which comprises a continuous light guide in place of the light. Additionally, a nose is provided on this second ring at the place where a nose is provided on the angle pieces which do not have a light.

This solution is possible because the slip rings in the angle pieces which have a light source therein must be easily removable from the angle piece by the dentist himself and likewise easily insertable again in the latter for the purpose of exchanging the light. Therefore, it is as easy for the dentist to exchange the coupling system, which is made possible according to the invention, as it was previously to change the light.

The invention results in a substantial reduction of storage, work preparation and delivery costs for the producers of the handpieces and angle pieces.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 shows a dental angle piece and a handpiece comprising a light source in a position immediately prior to or after coupling or uncoupling, respectively;

FIG. 2 shows a dental angle piece with light source and respective handpiece in a position analogous to that in FIG. 1;

DETAILED DESCRIPTION OF THE PREFERRED EMBODIMENTS

Figure 3:
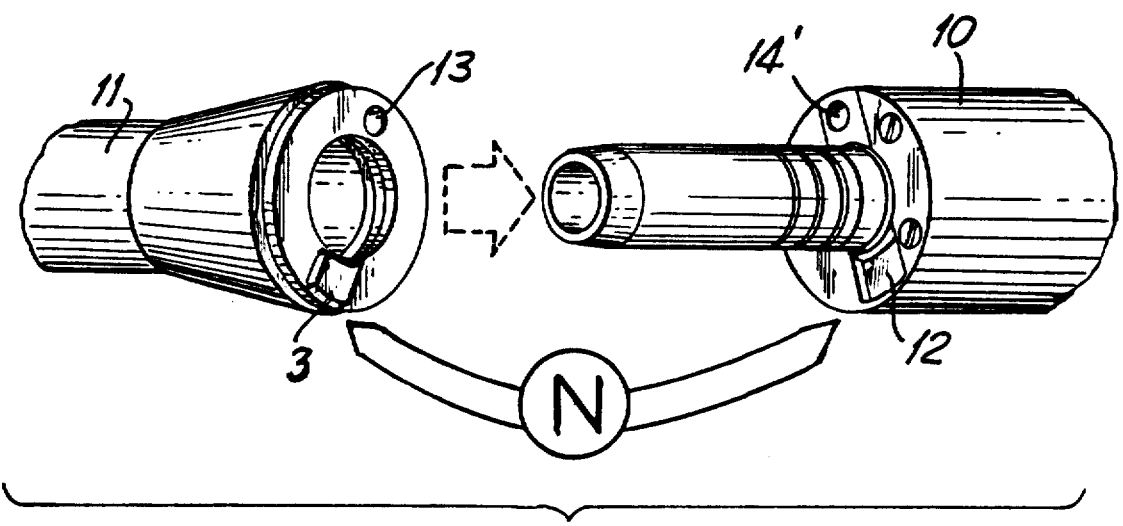
FIG. 3 shows an analogous view of FIG. 1, in perspective.

A conventional handpiece 10 - angle piece 11 combination 10, in which a light source 4, 4' is accommodated in the handpiece, is shown in FIG. 1. The position of the two parts relative to one another corresponds to a situation immediately prior to connection of the two or immediately after the disengagement of the connection. The light source 4, 4' can be accommodated directly in the coupling area or at the end of the handpiece 10 on the apparatus side, wherein, in the latter, case a light guide 14' guides the light from the source 4' to the coupling area 4.

A nose 3 in the coupling area of the angle piece 11 cooperates with a recess 12 in the handpiece 10 in such a way that the handpiece-side end 13 of the light guide 14 located in the angle piece 11 is located opposite the light source 4 or possibly opposite the angle-piece-side end of a light guide 14', respectively, in order to guide the light to the tool-side end 15 of the light guide 14 and, accordingly, to the work place.

FIG. 2 shows the second common construction, in which a light source 4" is provided in the angle piece 11. This light source is attached to a removable slip ring 2 and lies opposite the coupling-side end of a light guide 6. At the tool-side end 15, the light exits again from the light guide 6 in order to illuminate the operating area. The power supply for the light source 4" is effected via concentric conductors which are attached in the front of the slip ring 2 and via corresponding pins in the handpiece 10.

The couplings of the two systems correspond to one another with the exception of the described illumination device. In particular, the force transmission, the transmission of the cooling and rinsing fluid, etc. is identical in both types of coupling.

Figure 4:
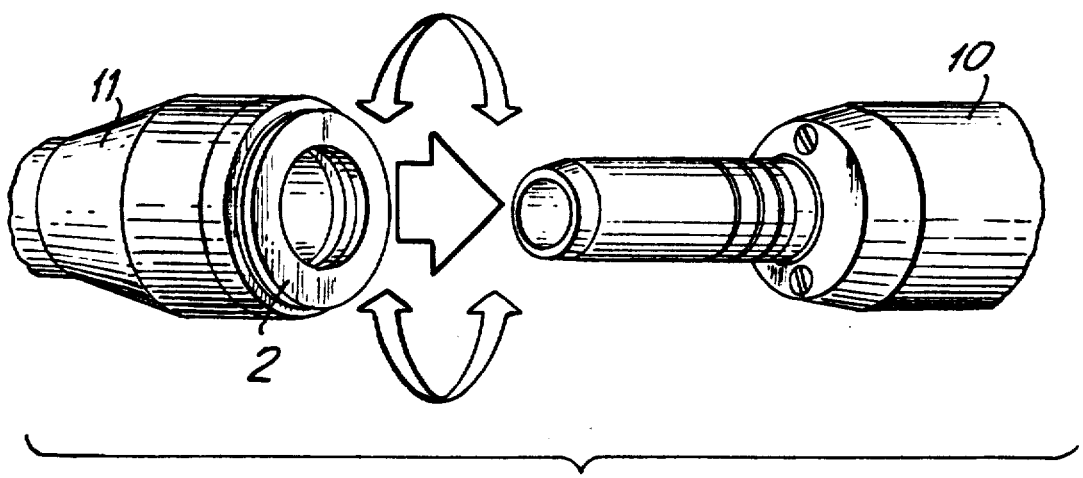
FIG. 4 shows an analogous view of FIG. 2 in perspective.

FIGS. 3 and 4 show the situation according to FIGS. 1 and 2 in a perspective view, wherein a handpiece 10 is shown in FIG. 3 which comprises a light guide 14'. The construction of the concentric conductor paths at the slip ring 2 on the front side can be clearly seen in FIG. 4.

The free turnability between the angle piece and the handpiece in the case of FIG. 4 and the locking with respect to rotation in the embodiment form according to FIG. 3 can additionally be seen.

Figure 5:
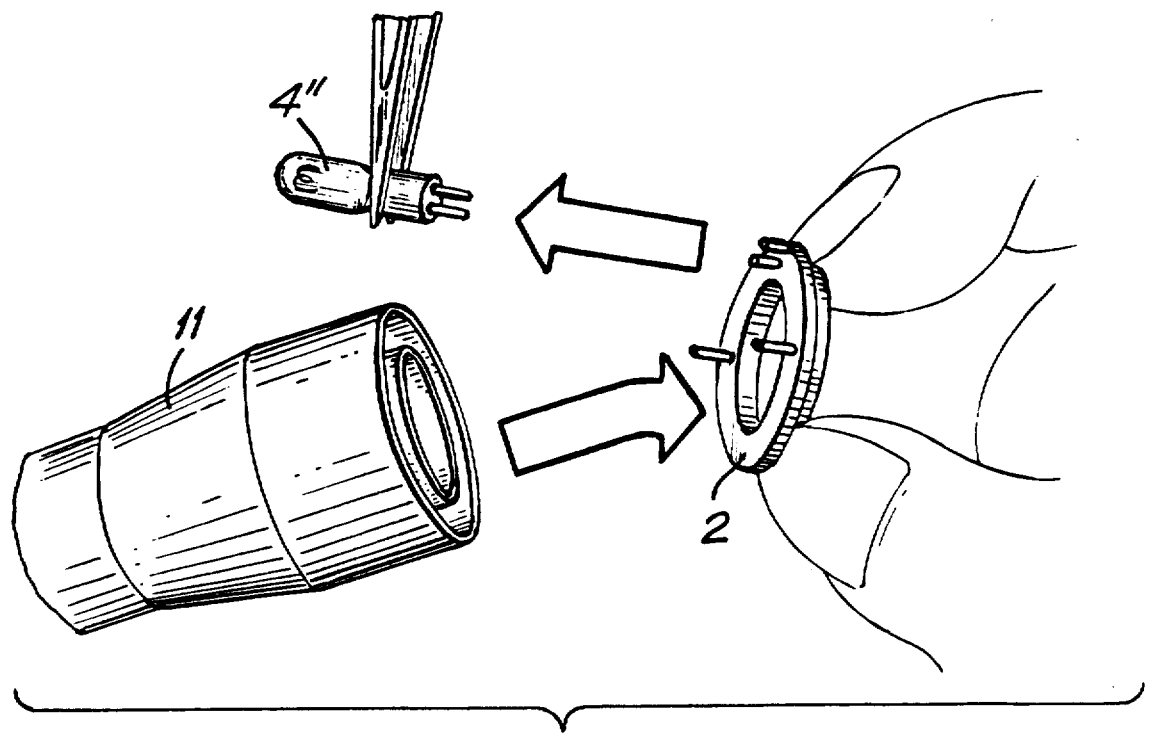
FIG. 5 shows exchanging of the light source when the latter is accommodated in the angle piece.

FIG. 5 shows the exchanging of a burnt-out light accommodated in the angle piece, which light is attached to the slip ring 2 of the angle piece 11. The invention makes use of this easy exchangeability of the slip ring 2 in that it uses a coupling ring 1, as shown in FIG. 6, which comprises a nose 3 in the area provided for it by the standard for light sources in the handpiece, and a piece of a light guide 5 is arranged in this area instead of a light 4'', which piece 5 transmits the light from the light source 4 or the light guide 14' in the handpiece, respectively, to the light guide 14 in the angle piece.

Figure 6:
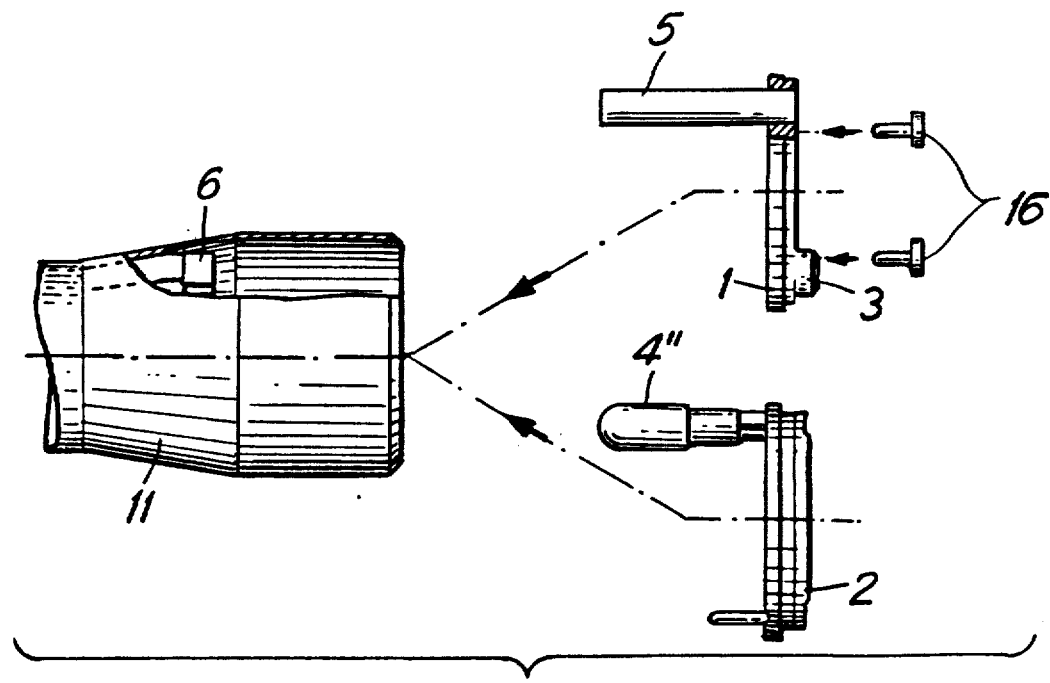
FIG. 6 shows the coupling ring, according to the invention, the slip ring carrying the light source, and its position with respect to the angle piece.

A more secure but still detachable connection between the coupling ring 1 and the angle piece 11 can possibly be provided by means of screws 16, which are shown in FIG. 6 so as to be rotated at an angle.

As can be seen from the view of the two rings 1, 2 which are shown next to one another, it is possible on the basis of the invention to produce uniform angle pieces 11 and to deliver the two rings 1, 2 along with them as accessories or to assemble them alternately in the plant, so that the two types of couplings on the handpiece side can be employed. For the manufacturer, this results in a substantial facilitation in production and storage and, for the user, in the possibility of freely exchanging the handpiece systems without also having to re-supply the entire angle pieces.

While the invention has been illustrated and described as embodied in an angle piece coupling, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters patent is set forth in the appended claims.

1. In a dental tool having a coupling connecting an angle piece with a handpiece wherein an outlet point for a light guide is provided in the angle piece near a tool holder in order to illuminate a work place in a patient's mouth and wherein a corresponding light source is provided in one of the angle piece and the handpiece, the light source being arranged as a projection on a slip ring which is removably attached to a coupling side of the angle piece, the improvement comprising:
   a second ring having a projection which is a continuous light guide in a location that corresponds to the location of the light source on said slip ring;
   a second projection providing a light guide nose on the second ring for mating engagement with a handpiece having said light source; and
   the slip ring being selectively interchangeable with the second ring so that different types of light sources are useable as needed and different supply hoses and motor parts are connectable to the angle piece.

2. An improved coupling according to claim 1, and further comprising screw means for fastening the slip or second ring at the angle piece.

* * * * *